United States Patent
McDonell (10) Patent No.: US 10,918,411 B2
(45) Date of Patent: Feb. 16, 2021

(54) VITRECTOMY PROBE WITH INTEGRAL VALVE

(71) Applicant: Novartis AG, Basel (CH)

(72) Inventor: Brian William McDonell, Irvine, CA (US)

(73) Assignee: Alcon Inc., Fribourg (CH)

( * ) Notice: Subject to any disclaimer, the term of this patent is extended or adjusted under 35 U.S.C. 154(b) by 271 days.

(21) Appl. No.: 15/934,146

(22) Filed: Mar. 23, 2018

(65) Prior Publication Data

US 2018/0206874 A1  Jul. 26, 2018

Related U.S. Application Data

(63) Continuation of application No. 14/090,235, filed on Nov. 26, 2013, now Pat. No. 9,924,963.

(60) Provisional application No. 61/736,641, filed on Dec. 13, 2012.

(51) Int. Cl.
  *A61B 17/3203*  (2006.01)
  *A61F 9/007*  (2006.01)
  *A61B 17/00*  (2006.01)

(52) U.S. Cl.
  CPC ...... *A61B 17/3203* (2013.01); *A61F 9/00736* (2013.01); *A61F 9/00763* (2013.01); *A61B 2017/00544* (2013.01)

(58) Field of Classification Search
  CPC .. A61F 9/00763; A61F 9/00736; A61F 9/007; A61F 9/00754; A61F 9/00825; A61F 9/0084; A61F 9/013; A61F 2009/00874; A61B 2017/00544; A61B 2017/0046; A61B 2017/0019; A61B 17/320016; A61B 17/32002; A61B 17/3203
  See application file for complete search history.

(56) References Cited

U.S. PATENT DOCUMENTS

| | | | |
|---|---|---|---|
| 2002/0173814 A1* | 11/2002 | Jung | A61F 9/00763 606/170 |
| 2011/0144675 A1* | 6/2011 | Gao | A61F 9/00736 606/167 |
| 2012/0158029 A1* | 6/2012 | Underwood | A61F 9/00763 606/171 |

* cited by examiner

*Primary Examiner* — Mohamed G Gabr (57) ABSTRACT

A vitrectomy apparatus for performing an ocular surgery may include a vitrectomy probe body graspable by a user and a cutter extending from the body and comprising an inner tube and an outer tube. The inner tube may be moveable relative to the outer tube. The apparatus also may include an actuator within the body and configured to actuate the inner tube relative to the outer tube. A valve may be carried by the body and may be configured to selectively direct a pressurized fluid to the actuator to actuate the inner tube relative to the outer tube.

9 Claims, 8 Drawing Sheets

VITRECTOMY PROBE WITH INTEGRAL VALVE

PRIORITY CLAIM

This application:

(a) is a continuation application of U.S. patent application Ser. No. 14/090,235 titled "Vitrectomy Probe with Integral Valve" which was filed Nov. 26, 2013 whose inventor is Brian William McDonell which is hereby incorporated by reference in its entirety as though fully and completely set forth herein, and (b) claims the benefit of priority of U.S. Provisional Application Ser. No. 61/736,641 (U.S. patent application Ser. No. 14/090,235 claimed the benefit of priority of provisional application Ser. No. 61/736,641 titled "Vitrectomy Probe with Integral Valve" filed on Dec. 13, 2012, whose inventor is Brian William McDonell), which is also hereby incorporated by reference in its entirety as though fully and completely set forth herein.

BACKGROUND

The present invention pertains to vitrectomy probes, systems, and methods. More particularly, but not by way of limitation, the present invention pertains to vitrectomy probes, systems, and methods utilizing an integral valve.

Microsurgical procedures frequently require precision cutting and/or removing various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g. cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. These cutting probes typically include a hollow outer cutting member, a hollow inner cutting member arranged coaxially with and movably disposed within the hollow outer cutting member, and a port extending radially through the outer cutting member near the distal end thereof. Vitreous humor and/or membranes are aspirated into the open port, and the inner member is actuated, closing the port. Upon the closing of the port, cutting surfaces on both the inner and outer cutting members cooperate to cut the vitreous and/or membranes, and the cut tissue is then aspirated away through the inner cutting member.

Conventional vitrectomy cutting probe systems include an actuation valve disposed within a console. Long drive lines connect to the actuation valve and to the cutting probe itself. Fluidic pressure through the actuation valve in the console and through the drive lines opens and closes the cutting port on the cutting probe.

Testing and field experience indicates that high vitrectomy probe cut rates result in reduced traction and reduced motion in the eye. However, in current systems, the cut rate capacity may be limited by the structure of the vitrectomy probe systems.

The present disclosure is directed to addressing one or more of the deficiencies in the prior art.

SUMMARY

In an exemplary aspect, the present disclosure is directed to a vitrectomy apparatus for performing an ocular surgery. The apparatus may include a vitrectomy probe body graspable by a user and a cutter extending from the body and comprising an inner tube and an outer tube. The inner tube may be moveable relative to the outer tube. The apparatus also may include an actuator within the body and configured to actuate the inner tube relative to the outer tube. A valve may be carried by the body and may be configured to selectively direct a pressurized fluid to and from the actuator to actuate the inner tube relative to the outer tube.

In one aspect, the valve comprises a fluidic piloted valve. In an aspect, the actuator comprises a first chamber and a second chamber separated by a diaphragm, and wherein the fluidic piloted valve actuates between a first position that directs pressurized fluid to the first chamber while venting the second and a second position that directs pressurized fluid to the second chamber while venting the first.

In another exemplary aspect, the present disclosure is directed to a vitrectomy apparatus for performing an ocular surgery. The apparatus may include a vitrectomy probe, where the vitrectomy probe may include a body graspable by a surgeon for performing the ocular surgery, a cutter configured to aspirate tissue, an actuator for driving the cutter, and a piloted valve carried by the body and actuatable to control the flow of pressurized fluid to and from the actuator. The apparatus also may include a pressure pulse generator disposed remotely from the vitrectomy probe. The pressure pulse generator may be arranged to generate a pulsing pilot signal. The apparatus also may include a fluid line extending between the piloted valve and the pressure pulse generator, where the fluid line carries the pulsing pilot signal to the piloted valve.

In another exemplary aspect, the present disclosure is directed to a method for driving a vitrectomy probe. The method includes pressurizing fluid in a supply line extending to a fluid actuator arranged to drive a cutter on the vitrectomy probe, generating a fluidic pilot signal remotely from the vitrectomy headpiece, and actuating a valve on the vitrectomy probe with the fluidic pilot signal to selectively direct the pressurized fluid into and out of a chamber of the fluid actuator.

In one aspect, generating the fluidic pilot signal comprises actuating a fluidic valve to generate a pulsing fluidic pilot.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure is directed to a surgical devices, systems, and methods for performing ophthalmic surgeries. The surgical system is arranged and configured to use a drive system that includes a valve disposed at a vitrectomy probe. This arrangement permits high pressure fluid to be supplied to the vitrectomy probe and cycled proximate the vitrectomy probe. Because the high pressure is cycled proximate the vitrectomy probe, it may provide a higher potential power source in the valve than is achieved when cycling the pressure at the console.

In addition, controlling the fluid flow with a valve at the vitrectomy probe may increase the pressures present in the actuator of the probe and reduce the quantity of fluid required. This reduced fluid requirement may be due to not varying the pressure in the supply lines over the full length. The higher pressures may permit the size of the actuator be reduced while producing the same forces. With these reduced flow requirements, the size of the tube delivering the fluid to the vitrectomy probe could be reduced. This may lead to a faster response time, resulting in potentially higher cut rates than can be obtained in conventional systems. Further, these faster probe cut rates may result in reduced traction and reduced motion in the eye.

Figure 1:
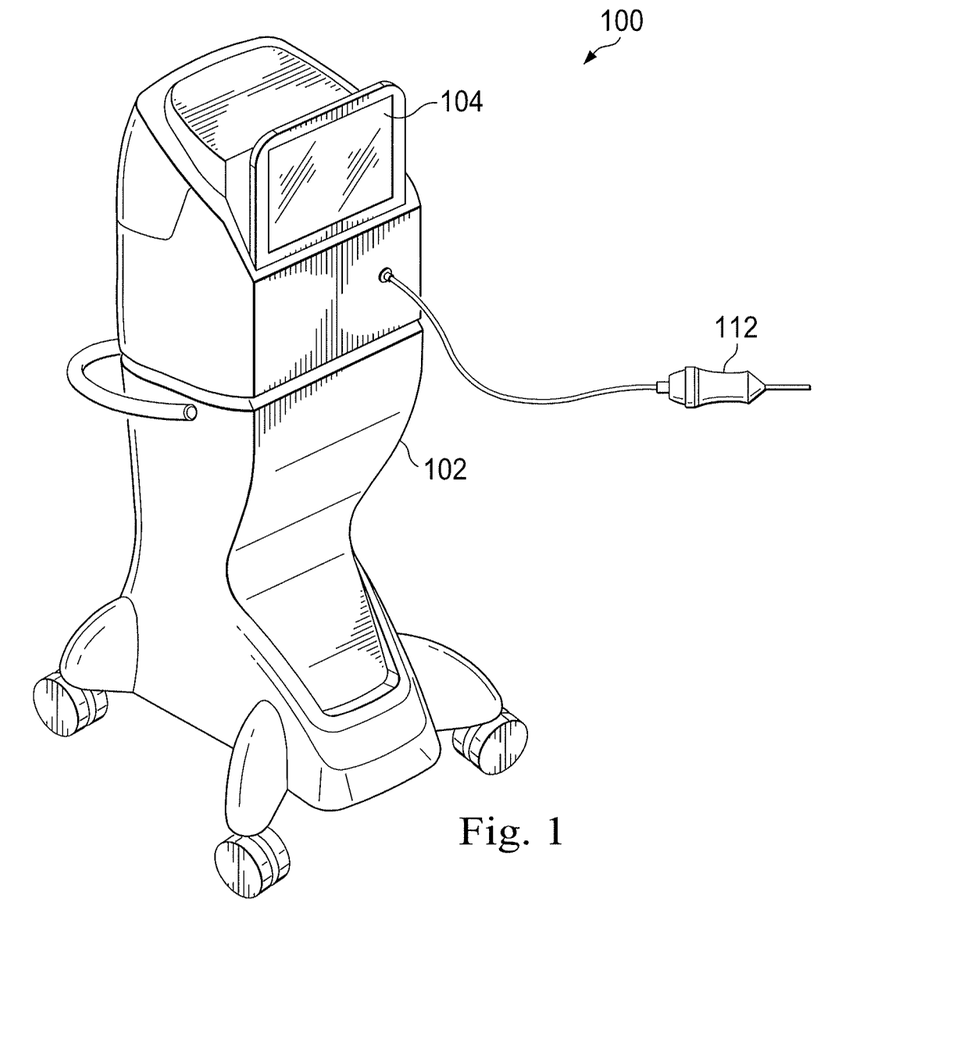
FIG. 1 is an illustration of an exemplary surgical system according to one aspect of the present disclosure implementing the principles and methods described herein.

FIG. 1 illustrates a vitrectomy surgical system, generally designated 100, according to an exemplary embodiment. The system 100 includes a base housing 102 and an associated display screen 104 showing data relating to system operation and performance during a vitrectomy surgical procedure. The surgical system 100 includes a vitrectomy probe 112 having an associated valve disposed therein.

Figure 2:
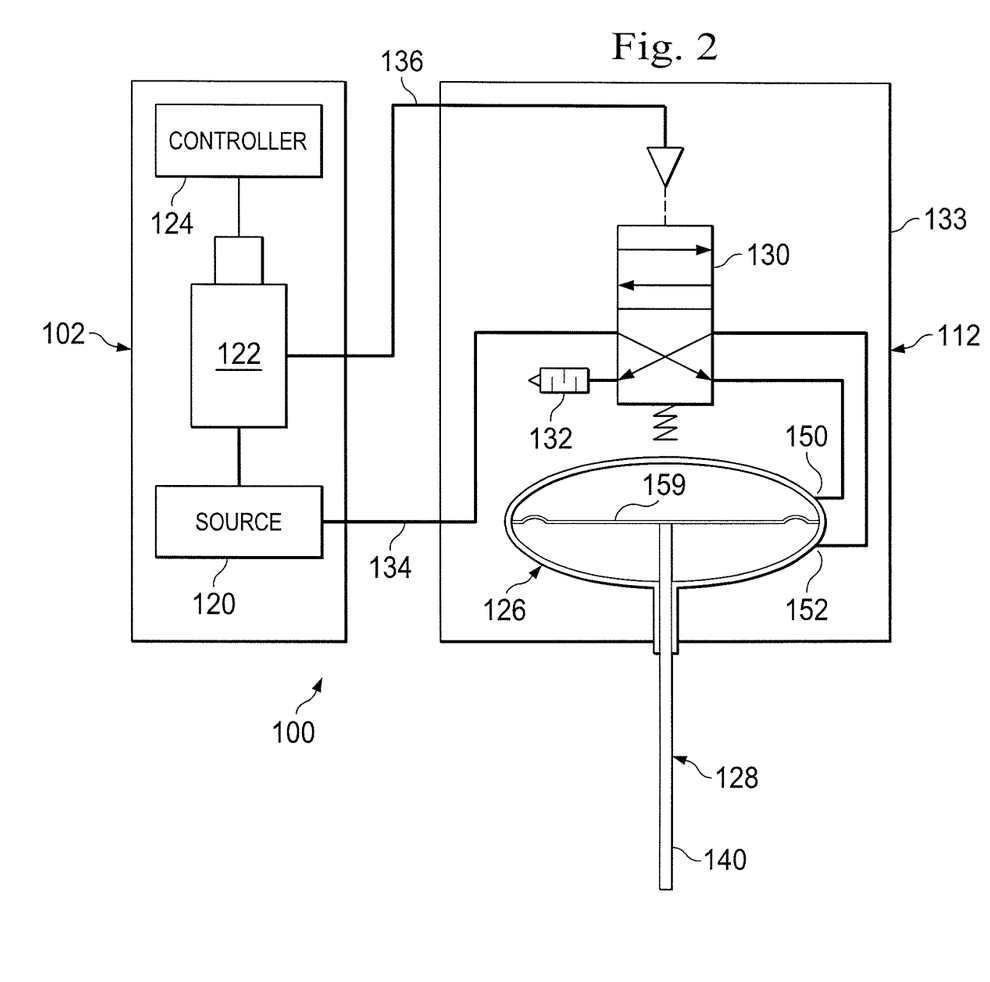
FIG. 2 is a diagram of aspects of the surgical exemplary system of FIG. 1 according to one aspect of the disclosure.

FIG. 2 is a block schematic diagram showing components of the vitrectomy surgical system 100 according to one exemplary embodiment. In FIG. 2, the system 100 includes the base housing 102 and the vitrectomy probe 112. The housing 102 includes a fluidic pressure source 120, a probe driver shown as a pressure pulse generator 122, and a controller 124.

The pressure source 120 is a high pressure tank and compressor that provides driving fluidic power to drive the vitrectomy probe 112. Some exemplary pressure sources are pneumatic pressure sources arranged to provide compressed air to drive the vitrectomy probe 112. In some embodiments, it is contained on the base housing 102, while in other embodiments; the pressure source is disposed elsewhere in or about the operating room.

The pressure pulse generator 122 is a standard three-way valve. The pressure pulse generator 122 has a solenoid that operates the driver between the charge and discharge positions under the control of the controller 124. As will become more apparent in the discussion below, the pressure pulse generator 122 cycles to set the cutting rate of the vitrectomy probe 112.

The controller 124 is in electrical communication with the pressure pulse generator 122 and configured to send control signals that control its actuation. The controller 124 may include a processor and memory that may include one or more executable programs that operates the pressure pulse generator 122 according to settings by the user or according to pre-established parameters.

The vitrectomy probe 112 includes a motor or an actuator 126, a cutter 128, an integral piloted valve 130, and a muffler 132. In the embodiment shown, these are all at least partially disposed within a hand-graspable handle body 133 configured to be carried in the hand of a surgeon.

As can be seen, the fluidic pressure source 120, the pressure pulse generator 122, and the piloted valve 130 on the vitrectomy cutter 112 are in fluid communication with each other along lines representing flow paths or flow lines. In this embodiment, a supply line 134 and a control or pilot line 136 extend between the base housing 102 and the vitrectomy probe 112. The supply line 134 carries a constant pressurized fluid for driving the actuator 126 as will be described below. In some exemplary embodiments, the supply line maintains a pressure greater than 20 psi (pounds per square inch), while in other exemplary embodiments, the supply line maintains a pressure greater than 30 psi. In some embodiments, the supply line pressure is greater than 40 psi. The pilot line 136 fluidically controls the piloted valve 130 to direct pressured fluid in the supply line 134 to and from the actuator 126. A vacuum line (not shown) also extends from the housing to the vitrectomy probe 112 and is used to aspirate fluid and tissue from the cutter.

In this embodiment, the actuator 126 is a fluidic actuator having a hollow interior formed of an inner chamber divided into first and second chambers by a reciprocating fluid driven diaphragm 159. First and second ports 150 and 152 provide fluid access to the actuator 126. The fluidically driven actuator 126 operates by receiving fluidic pressure alternating through the first and second ports 150 and 152 which corresponds to the first and second chambers of the actuator 126. In some embodiments, the fluidic actuator is air-powered or pneumatic actuator.

As can be seen, the cutter 128 extends from the handle body 133 and includes a distal end 140. It includes an outer cutting tube 156, an inner cutting tube 158, and a probe actuator or motor shown in FIG. 2. The cutter operation is discussed in greater detail with reference to FIG. 3.

Figure 3:
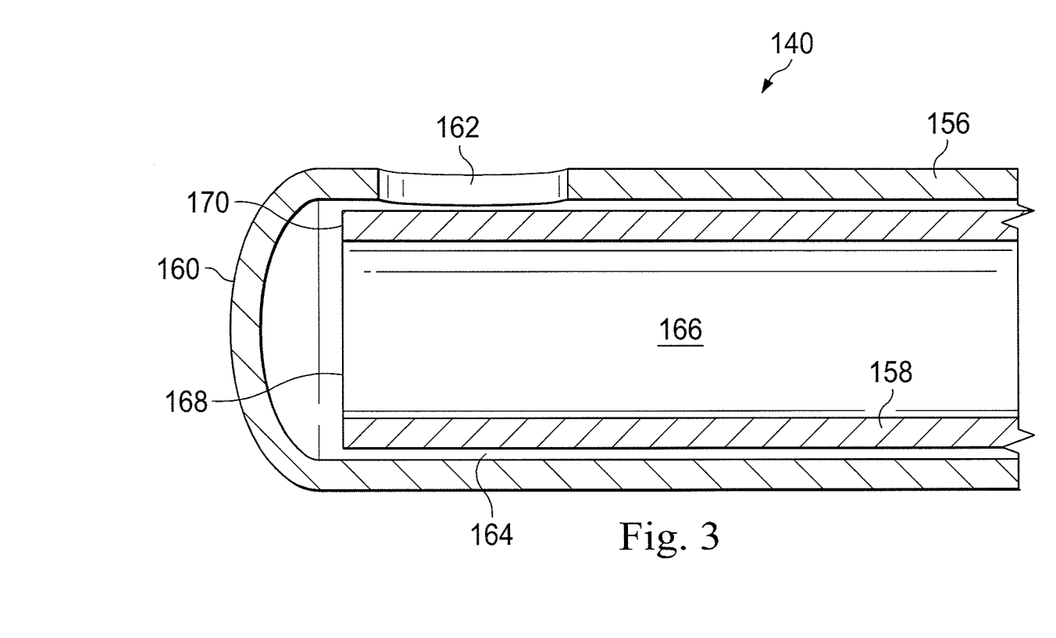
FIG. 3 is an illustration of a distal end of a cutter of an exemplary vitrectomy probe in cross-section operable in accordance with the principles and methods described herein.

FIG. 3 shows the distal end 140 of the cutter 128 in greater detail. The cutter 128 includes the outer cutting tube 156 that has a closed end 160, and an outer port 162 that receives tissue, such as ophthalmic tissue. The outer port 162 is in fluid communication with an inner channel 164 of the outer cutting tube 156. The inner cutting tube 158 is located within the inner channel 164 of the outer cutting tube 156. The inner cutting tube 158 has an inner bore 166, an open end 168, and a cutting surface 170. The inner bore 166 is in fluid communication with an aspiration line (not shown) that connects to a vacuum pressure that pulls tissue into the outer port 162 when the inner cutting member 158 is located away from the port 162. The inner cutting tube 158 moves within the inner channel 164 of the outer cutting tube 156 to cut tissue that is pulled into the outer port 162 by the aspiration system. The ophthalmic tissue received by the outer port 162 is preferably vitreous or membranes.

When used to cut tissue, the inner cutting tube 158 is initially moved away from the outer port 162 and the vacuum pressure pulls tissue into the port 162 and the inner channel 164. The inner cutting tube 158 then moves toward the outer port 162 and severs the tissue within the inner channel 164. The severed tissue is pulled through the inner bore 166 of the inner cutting tube 158 by the aspiration system. The inner cutting tube 158 then moves away from the outer port 162, and the cutting process is repeated. A cutting cycle includes moving the inner cutting tube 158 to open the port 162 and then moving the cutting tube 158 to close the port 162 to initiate the cut and return the cutting tube 158 to its starting position for the next cutting cycle.

With reference now to both FIGS. 2 and 3, the inner cutting tube 158 is driven by fluid pressure directed on opposing sides of the diaphragm 159. In one example of operation, if fluid pressure is increased at the first port 150, the diaphragm 159 will move distally, displacing the inner cutting tube 158 relative to the outer cutting tube 156, thereby closing the tissue-receiving port 162 of the outer cutting tube 156. This cuts any vitreous material which may have been aspirated into the tissue-receiving outer port 162. Venting the pressure at the first port 150 and increasing the pressure at the second port 152 will move the diaphragm 159 proximally, opening the tissue-receiving outer port 162 so that it can draw in new vitreous material to be cut. Its worth noting that other embodiments include alternative probe actuators. For example, some embodiments include a fluidically driven piston motor in place of a diaphragm.

Returning to FIG. 2, in the example shown, the piloted valve 130 is a standard four-way valve that alternatingly directs pressurized flow to the first and second ports 150, 152 of the actuator 126 while simultaneously venting the other port. The piloted valve 130 is actuated between its positions by pilot pressure pulses sent or created by the pressure pulse generator 122. When in the position shown in FIG. 2, the piloted valve 130 is in a position to provide fluidic pressure to the first port 150, and to vent fluidic pressure from the second port 152. In this position, fluidic pressure can pass from the pressure source 120, through the piloted valve 130, and to the first port 150 where the fluidic pressure provides fluidic power to the vitrectomy probe. At the same time, fluidic pressure at the second port 152 can pass through the piloted valve 130 to the muffler 132 where it is exhausted to the atmosphere. In the other position, the piloted valve 130 allows fluidic pressure to pass from the pressure source 120 to the second port 152 where the fluidic pressure provides fluidic power to the vitrectomy probe 112. At the same time, fluidic pressure at the first port 150 can vent through the piloted valve 130 to the muffler 132 where it is exhausted to the atmosphere. In this embodiment, the piloted valve 130 operates based on fluidic pressure pulses in the pilot line 136.

In this embodiment, the muffler 132 is disposed within the probe 112. Because of this, the exhaust passage from the actuator to the muffler is very short, and may reduce pressure-back-up during the exhaust process. Reducing the exhaust back-up may result in a faster exhaust, enabling a faster response time and the possibility of an increased cutting rate. In other embodiments however, the muffler 132 is disposed at the console 102 or elsewhere in the surgical system 100. If a fluid other than air is used, the system may include a return line extending to the console. The return line may be a reusable line associated with the console.

While conventional systems use actuation valves at the console or base housing 102, such valves may suffer from some drawbacks, as the pressure pulses created by the valves must travel long distances through the tubing from the console to the probe actuator. To effectively drive the actuator, and in order to fill the volumes of the actuator adjacent the diaphragm, the pressure must be maintained as relatively high. This requirement however, creates limits on the cut rate, since it takes relatively longer to alternate the actuator with higher pressure fluctuations that must travel longer distances. For example, the travel distance may result in less distinct pulses, which slows response times and requires greater spacing between pulses. In addition, because the high pressure is cycled proximate the vitrectomy probe, it may provide a higher potential power source in the actuator than is achieved when cycling the pressure at the console. In one example, a 50 psi pressure differential will be available at the vitrectomy probe between the supply pressure and atmosphere. In contrast, some pressure differentials in conventional systems at the end of the drive lines at 7,500 cycles per minute may be only 8 psi, even when measured without any "load" or work being done at the end of the tube which would reduce the pressure further. In addition, the arrangement disclosed herein may achieve faster cut rates because the pressure to drive the piloted valve 130 may be minimized, and as such, the volume of fluid to actuate the valve 130 can be less than the volume of fluid to actuate the actuator 126. Therefore, the valve 130 can be actuated faster using the pilot line than a conventional valve in the console, set up to drive the actuator in the vitrectomy cutter.

Here, in use, the pressure pulse generator 122 provides fluidic pilot pressure along the pilot line to drive the piloted valve 130. Actuation of the pressure pulse generator 122 results in a pulsing pressure at the pilot line and the piloted valve 130. The pulses correspond to the cut rate. Because the fluidic pilot control signal is only actuating the piloted valve, instead of actuating the actuator 126, the pilot control signal may have reduced pressure and flow requirements (compared to the probe actuator) as it would only be moving the piloted valve 130, not the full cutter assembly with its seals and other friction sources. This reduced pressure and flow requirement allows the signal or pilot line to be pulsed at higher frequencies than can be achieved with a conventional arrangement where the signal or pilot line directly powers the entire actuator of the vitrectomy probe. In addition, the piloted valve 130 does not need to maintain tight sealing between its ports. In some embodiments, the piloted valve 130 is designed with expected leakage in exchange for low friction. This may result in faster actuation response. In addition, because of the low flow requirements, this piloted valve 130 could be small, enabling actuation with a minimal volume shift of fluid, also contributing to a potentially higher cut rate.

At the same time that the piloted valve 130 is being actuated by relatively low pressure fluidic pulses, the supply pressure is maintained at a relatively higher pressure sufficient to actuate the actuator 126 because of its continuous exposure to the source 120.

Although the above system is described as having a fluidic valve in the probe, it is recognized that an electric valve, driven by a controller may also be incorporated within the probe. However, since some embodiments of the vitrectomy probe are single use probes, the cost of the probes may increase dramatically if each single-use device includes an electrically driven solenoid valve.

Figure 4:
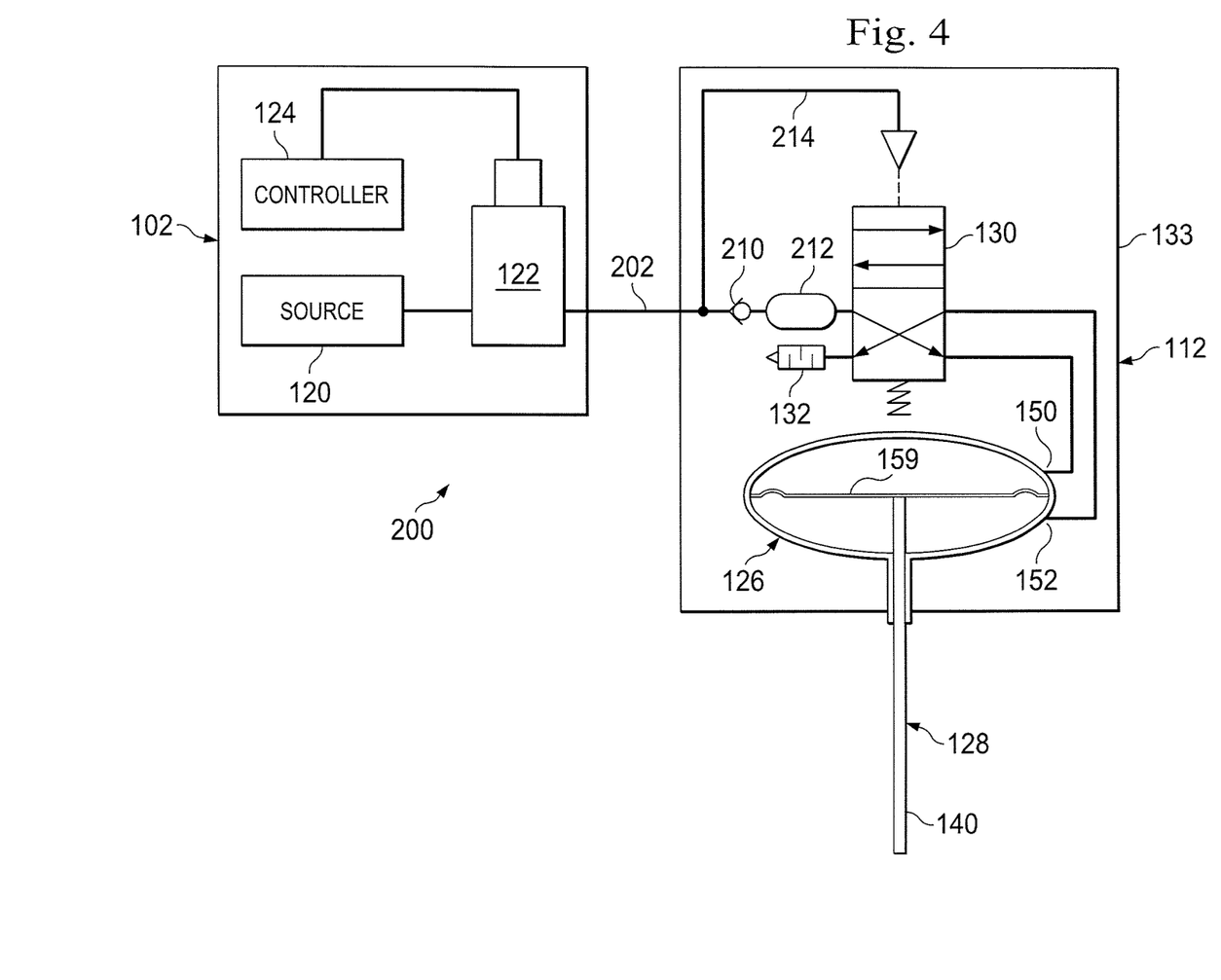
FIG. 4 is a diagram of additional aspects of an exemplary system according to one aspect of the disclosure.

FIG. 4 is a block diagram of an alternative surgical system, referenced herein by the numeral 200. The system 200 includes a control signal line superimposed on the supply pressure line, referenced as the supply pressure line 202. In this embodiment, the console 102 includes the pressure pulse generator 122, the controller 124, and the source 120. The probe 112 includes the actuator 126, the cutter 128, the piloted valve 130, and the muffler 132. In this embodiment, the probe includes a one-way check valve 210 and an accumulator 212. Here, a pilot line 214 intersects the supply pressure line 202 before the check valve 210.

In this example, the supply line 202 is maintained at a high pressure, so that when the piloted valve 130 opens, there is immediate high pressure to invoke a faster response time at the probe actuator 126.

In this embodiment, the one-way check valve 210 is disposed between the pilot line 214 and the accumulator 212, which is disposed directly adjacent the piloted valve 130. The accumulator 212 is configured to absorb the pilot pulses sent down the supply line 202 so that the pressure available to the actuator 126 through the piloted valve 130 remains relatively stable. Other embodiments include a fluid-restricting orifice on the inlet to the accumulator.

In this embodiment, the supply pressure line 202 is a continuous pressure in the supply tube with a pressure fluctuation to control actuation. In this case, the pressure threshold at which the valve pilot actuates would be raised and may be for example, within a range of about 35 psi to 45 psi. It is possible that the single line configuration would have a reduced performance relative to the separate line configuration shown in FIG. 2, but would reduce the tube count and still may provide sufficient functionality, by having the piloted valve at the probe and having the continuous high pressure line at the piloted valve to increase the cutting rate based on the continuous higher pressure at the actuator 126.

In this embodiment, the source 120 provides a high pressure fluidic fluid to the pressure pulse generator 122. The controller 124 controls the pressure pulse generator 122 to pulse the high pressure flow through the pressure line 202. In this example, the controller controls the pressure pulse generator 122 to oscillate at the desired cut rate between an upper high pressure limit and a lower high pressure limit. In one example, the pressure pulse generator 122 oscillates the high pressure between an upper high pressure limit of about 35 psi and a lower high pressure limit of about 25 psi. Other pressure levels are contemplated.

The piloted valve 130 is configured to actuate at a pressure between the high pressure and lower pressure limits. For example, when the upper high pressure limit is about 35 psi and the lower high pressure limit is about 25 psi, then the piloted valve actuation pressure may be, for example, an average of these at about 30 psi. Accordingly, the piloted valve 130 transitions each time the pressure fluctuates past the piloted valve actuation pressure. As such, as the pressure pulse generator 122 drives the pressure fluctuations, the piloted valve 130 then actuates at the desired cutting rate. At the same time, the high pressure fluctuations are absorbed by the accumulator 212 to provide a relatively stable supply pressure through the piloted valve 130 to the actuator 126.

The cut rate may be increased over conventional systems however because the responsiveness to the valve is dramatically increased due to the proximity of the piloted valve 130 to the actuator 126. That is, the directional changes of the actuator can be accomplished very quickly because a high pressure is maintained in the supply line at all times.

Figure 5:
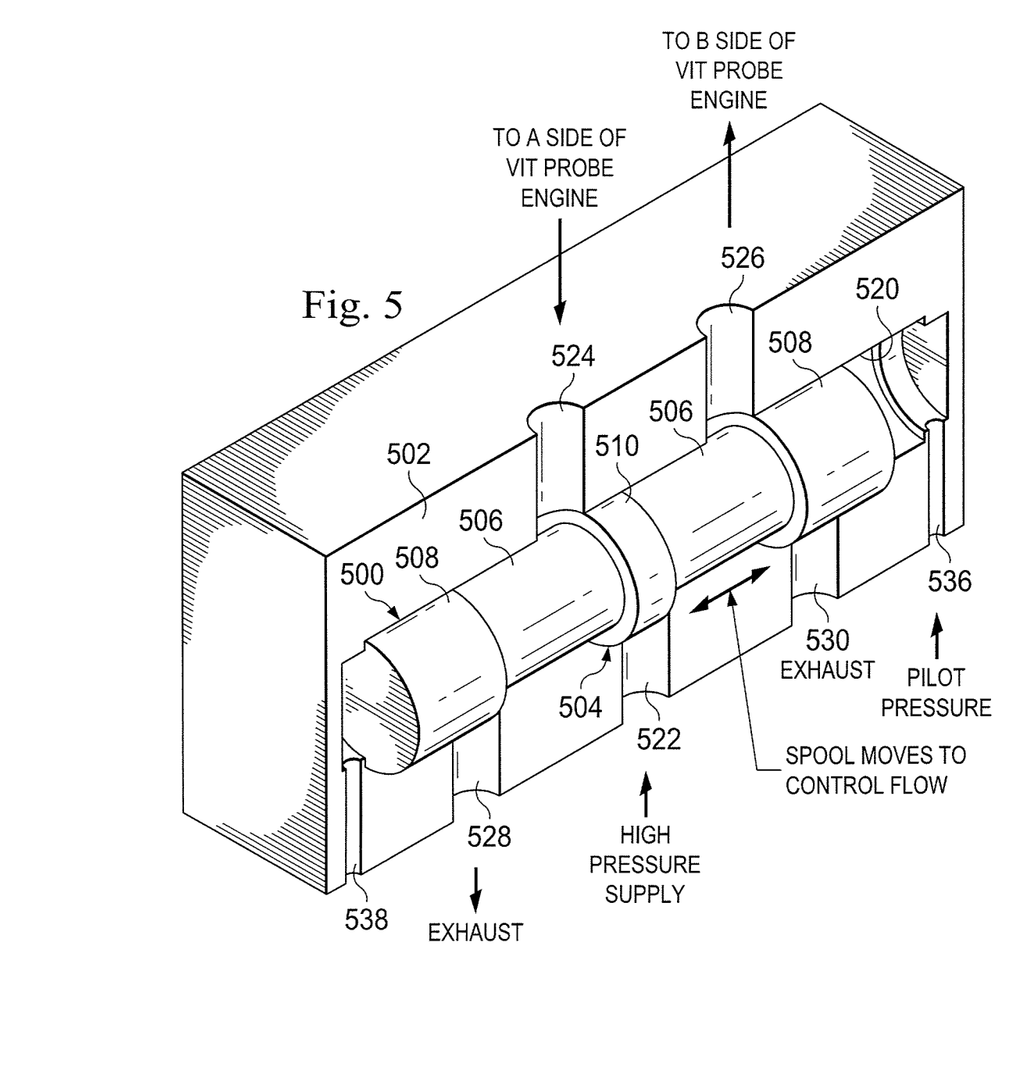
FIG. 5 is an illustration of a portion of an exemplary double piloted valve according to one aspect of the present disclosure implementing the principles and methods described herein.
Figure 6:
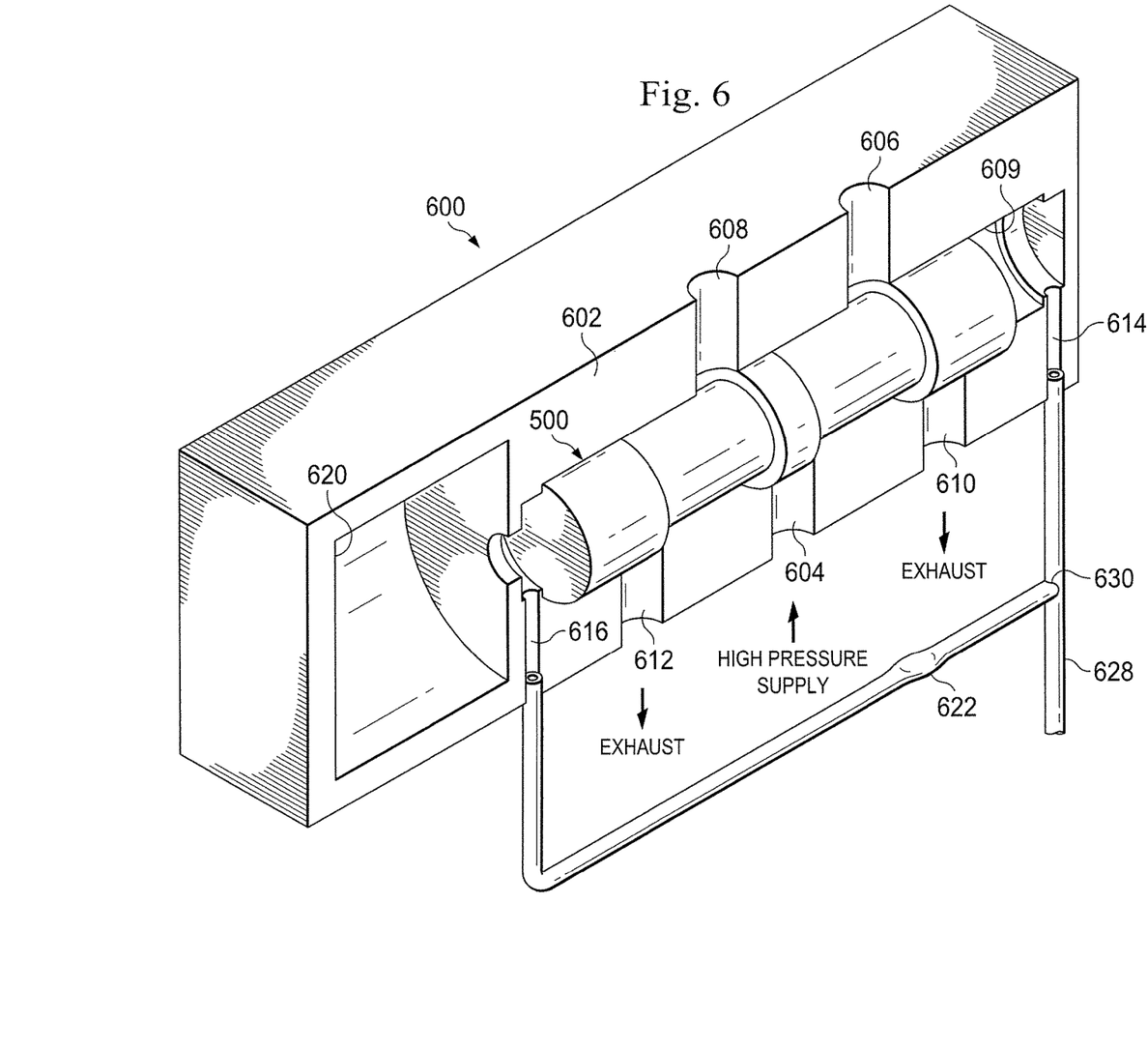
FIG. 6 is an illustration of a portion of an exemplary double piloted valve and system according to one aspect of the present disclosure implementing the principles and methods described herein.

The exemplary valves discussed above are single pilot valves with spring returns. FIGS. 5 and 6 show exemplary implementations of a double-piloted valve (two fluidic control inputs). These include exemplary spools and arrangements that may be used in the piloted valves discussed above, or may be used in alternative piloted valves. In the two embodiments shown, the piloted valves are five-way valves that may be used as a part of the piloted valves discussed above and as alternatives to the four-way valves shown.

FIG. 5 shows a spool 500 in a base 502 forming a part of a piloted valve usable in the systems discussed above. In this embodiment, the spool 500 has a longitudinal axis and includes larger diameter regions 504 and smaller diameter regions 506. The larger diameter regions include exhaust plug regions 508 and a central separator 510.

In FIG. 5, the base 502 is designed to have a chamber 520 which houses the spool 500 and permits the spool 500 to longitudinally slide back and forth under pressure. A single high pressure supply port 522 leads to the chamber, and two outlet ports 524, 526 lead from the valve chamber 520 to the different chambers of the actuator 126. In addition, two exhaust passages 528, 530 lead from the chamber 520 to the muffler 132 (shown in FIG. 2, for example).

Two pilot ports 536, 538 are also formed in the base 502 and are disposed to provide pilot pressure on ends of the spool 500 in a manner that moves the spool 500 back and forth within the valve chamber 520. The pilot ports 536, 538 are attached to the control or pilot line, while the pressure supply port 522 connects to the supply line. In this example, the valve is a double-acting valve that is actuated by alternating pilot pressure. Accordingly, this embodiment includes two pilot lines that may be actuated by a valve disposed on the surgical console, for example. In some embodiments, as shown in FIG. 5, the spool may be free of seals in order to reduce friction, thereby exchanging expected leakage for low friction. This may result in faster actuation response. In addition, small chambers at the spool ends may enable valve switching even at low pressure volumes than can be achieved when driving a probe actuator, also contributing to an increased cut rate.

In another embodiment, the valve has only one pilot port. In place of the other pilot port, the valve includes a spring that biases the spool to a first position. For example, in this embodiment, the pilot pressure port 536 may be replaced with a spring that biases the spool to the position shown in FIG. 5. Pressure through the other pilot supply port 538 acts against the spool to displace the spool and compress the spring connecting ports 522 and 524 together. By pulsing the pilot pressure, the spool moves back and forth to alternate pressure the chambers of the actuator and drive the cutter.

Another embodiment of a piloted valve is shown in FIG. 6, and is referenced by the numeral 600. This embodiment includes the same spool 500 and includes a base 602. The base 602 includes a single high pressure supply port 604, two outlet ports 606, 608 that lead from a valve chamber 609 to the different chambers of the actuator 126. In addition, it includes two exhaust passages 610, 612 that lead from a chamber 609 to the muffler 132 (shown in FIG. 2, for example). Two pilot ports 614, 616 provide access to the ends of the spool 500.

Figure 7:
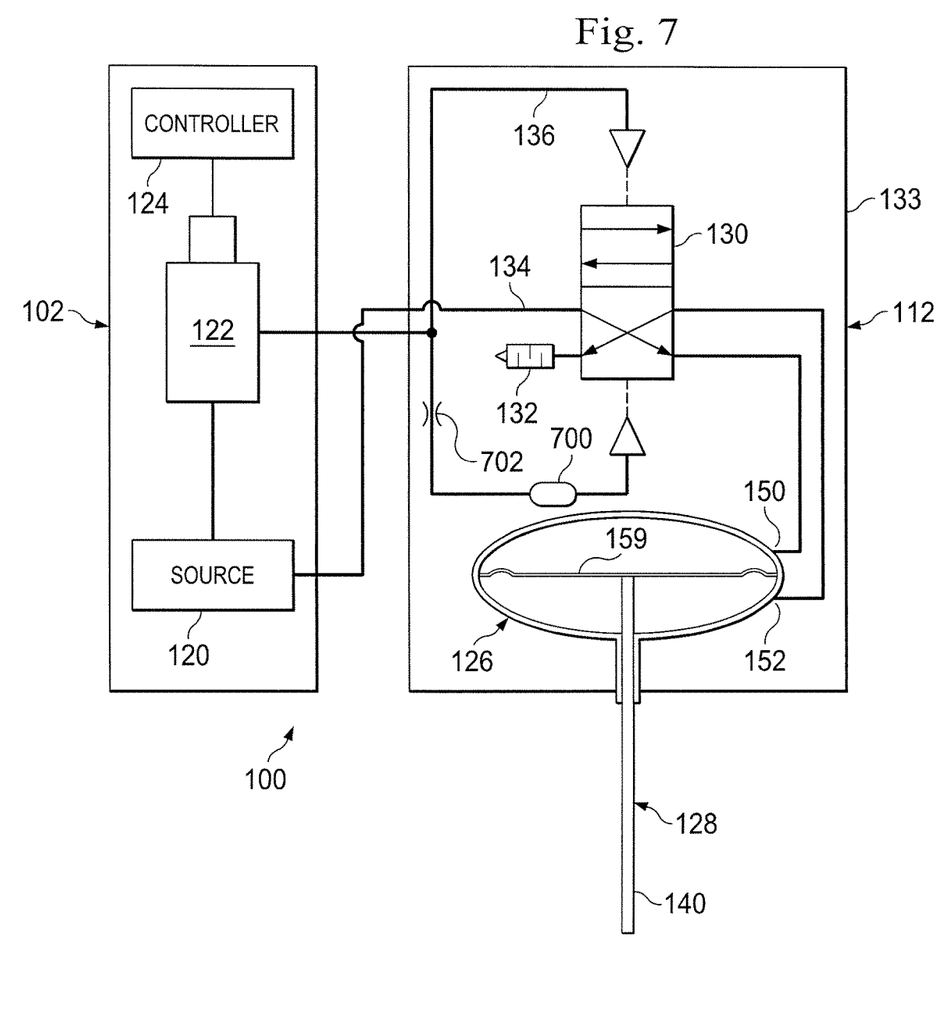
FIG. 7 is a diagram of exemplary additional aspects incorporating a valve as shown in FIG. 6 in an exemplary system such as that of FIG. 2 according to one aspect of the present disclosure implementing the principles and methods described herein.
Figure 8:
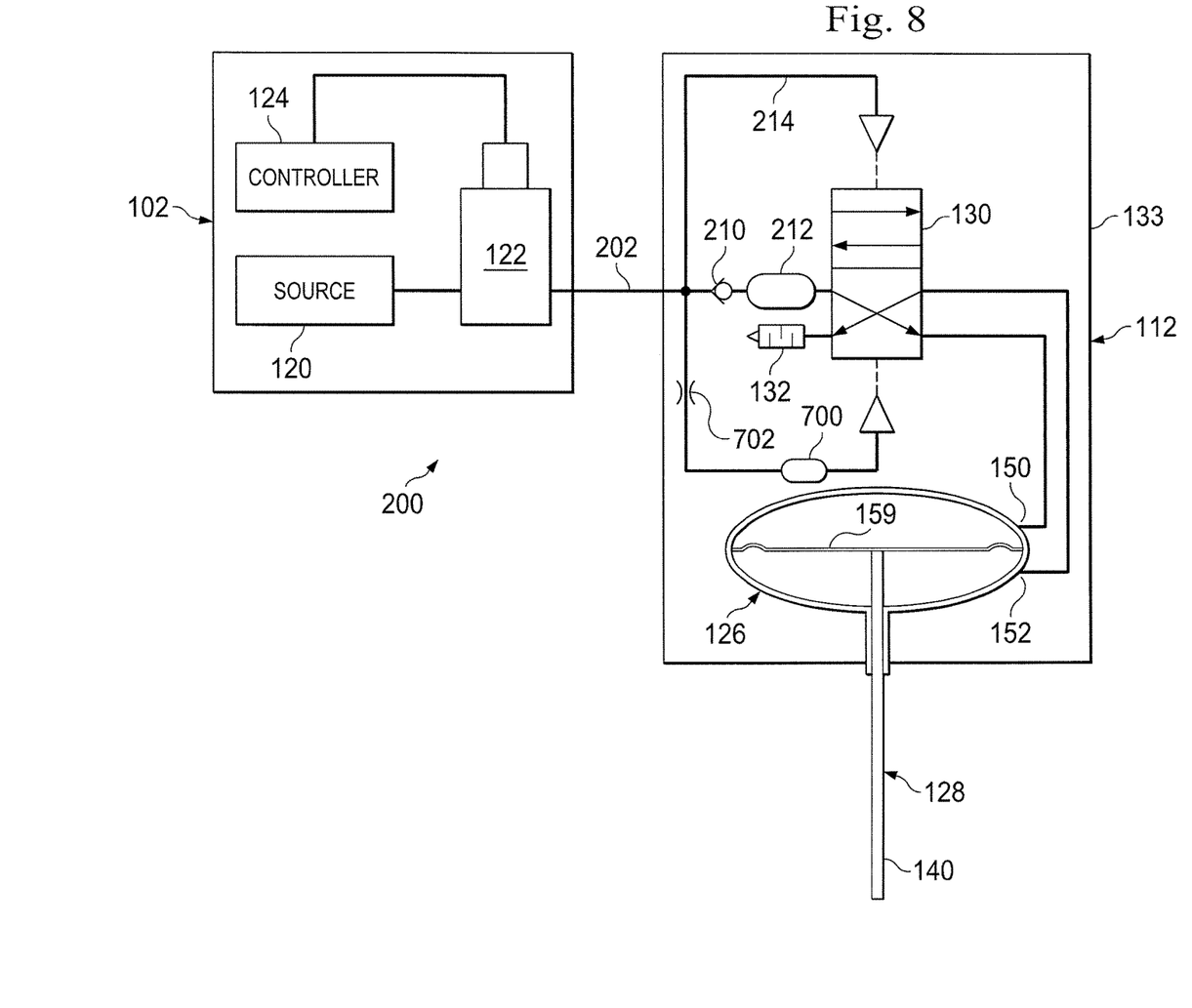
FIG. 8 is a diagram of exemplary additional aspects incorporating a valve as shown in FIG. 6 in an exemplary system such as that of FIG. 4 according to one aspect of the present disclosure implementing the principles and methods described herein.

In addition, the base 602 includes an accumulator pressure chamber 620 in communication with one of the pilot lines. In this example, the valve may operate with either two independent pilot lines or may operate with a single joined pilot line. FIG. 6 shows a single joined pilot line 628 that splits at a split point 630 to bring pressure to each pilot port 614, 616 and to each end of the spool 500. The split line includes a flow restrictor 622, shown as an orifice, for reducing the fluctuation of pressure to the pilot port 616. In cooperation with the accumulator, which may further dampen fluctuations, the pressure at the pilot port 616 may be relatively stable and may be at or around the average pressure of the pressure in the fluctuating pilot line 628. Accordingly, for example only, while the pressure at pilot port 614 may swing between 25 psi and 35 psi, the pressure at pilot port 616 may swing between 28 psi and 32 psi. When the pressure at the pilot port 616 is at 33 psi, the spool may slide toward the accumulator, and when the pressure at the pilot port 616 is at 27 psi, the spool may slide away from the accumulator. In this way the accumulator can serve as a self calibrating return force for the spool in lieu of a fixed force return spring. FIGS. 7 and 8 show a diagram of the systems of FIGS. 2 and 4 respectively modified to incorporate the piloted valve of FIG. 6. As can be seen, these each include an accumulator 700, which may be an accumulator such as the accumulator pressure chamber 620 in FIG. 6. These each also include an orifice or flow restrictor 702, which may be a flow restrictor such as the flow restrictor 622 in FIG. 6.

Although shown with a single pressure pulse generator 122, other embodiments include two pressure pulse generators, one associated with each of the two ports 536 and 538. These embodiments operate similar to the manner described, with the drivers being configured to independently receive operating signals from the controller 210. Yet other arrangements are contemplated.

According, piloted valves in the probe may be used to provide control and high pressure control to the vitrectomy probe to produce rapid changes in the actuator pressures required for high frequency action.

While the actuators described herein are double acting actuators, the same principles could be used on single-acting actuators. Further, in some embodiments, an electrical valve could be disposed within the probe in place of the piloted valve. Electrical connections and conductors would then need to be routed to the probe.

While the examples herein were described using pressure level changes, some embodiments have piloted valves that respond to pressure. This may provide robust and high performance.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

I claim:

1. A vitrectomy apparatus for performing an ocular surgery, comprising:
    a vitrectomy probe body graspable by a user;
    a cutter extending from the vitrectomy probe body and comprising an inner tube and an outer tube, the inner tube being moveable relative to the outer tube;
    a single high pressure supply line extending to the vitrectomy probe body from a pressurized fluid source remote from the vitrectomy probe body;
    an actuator within the vitrectomy probe body and configured to actuate the inner tube relative to the outer tube; and
    an electrical valve inside the vitrectomy probe body and configured to selectively direct a pressurized fluid, from the single high pressure supply line, to the actuator to actuate the inner tube relative to the outer tube;
    wherein the actuator comprises a first chamber and a second chamber separated by a diaphragm, and wherein the electrical valve actuates between a first position that directs the pressurized fluid to the first chamber while venting the second chamber and a second position that vents the first chamber while directing the pressurized fluid to the second chamber to reciprocate the inner tube back and forth within the outer tube.

2. The vitrectomy apparatus of claim 1, further comprising an electrical line coupled to a surgical console and the electrical valve inside the vitrectomy probe body, wherein an electrical signal from the electrical line actuates the valve.

3. The vitrectomy apparatus of claim 1, wherein the single high pressure supply line is pressurized to and maintained at more than 20 psi (pounds per square inch).

4. The vitrectomy apparatus of claim 1, further comprising an aspiration line extending from the body to a surgical console.

5. The vitrectomy apparatus of claim 1, wherein the pressurized fluid source is comprised in a surgical console remote from the vitrectomy probe body.

6. A vitrectomy apparatus for performing an ocular surgery, comprising:
    a vitrectomy probe comprising
        a body graspable by a surgeon for performing the ocular surgery,
        a cutter configured to aspirate tissue, the cutter comprising an inner tube and an outer tube, the inner tube being moveable relative to the outer tube,
        an actuator for driving the cutter, and
        an electrical valve inside the body and actuatable to control the flow of pressurized fluid to the actuator;
    a surgical console, remote from the vitrectomy probe, comprising a pressurized fluid source, wherein the pressurized fluid source is coupled to the electrical valve through a single high pressure supply line; and wherein the electrical valve is configured to selectively direct the pressurized fluid, from the single high pressure supply line, to the actuator to actuate the inner tube relative to the outer tube;

wherein the actuator comprises a first chamber and a second chamber separated by a diaphragm, and wherein the electrical valve actuates between a first position that directs the pressurized fluid to the first chamber while venting the second chamber and a second position that vents the first chamber while directing the pressurized fluid to the second chamber to reciprocate the inner tube back and forth within the outer tube.

7. The vitrectomy apparatus of claim 6, further comprising an electrical line coupled to the surgical console and the electrical valve that is inside the body, wherein an electrical signal from the electrical line actuates the valve.

8. The vitrectomy apparatus of claim 6, wherein the single high pressure supply line is pressurized to and maintained at more than 20 psi.

9. The vitrectomy apparatus of claim 6, further comprising an aspiration line extending from the body to the surgical console.

* * * * *